(12) United States Patent
Randers-Pehrson et al.

(10) Patent No.: US 10,369,379 B2
(45) Date of Patent: Aug. 6, 2019

(54) APPARATUS, METHOD, AND SYSTEM FOR SELECTIVELY EFFECTING AND/OR KILLING BACTERIA

(71) Applicant: THE TRUSTEES OF COLUMBIA UNIVERSITY IN THE CITY OF NEW YORK, New York, NY (US)

(72) Inventors: Gerhard Randers-Pehrson, Ossining, NY (US); David Jonathan Brenner, New York, NY (US); Alan Bigelow, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 14/886,635

(22) Filed: Oct. 19, 2015

(65) Prior Publication Data
US 2016/0107000 A1    Apr. 21, 2016

Related U.S. Application Data

(60) Division of application No. 14/021,631, filed on Sep. 9, 2013, now Pat. No. 10,071,262, which is a
(Continued)

(51) Int. Cl.
*A61N 5/06* (2006.01)
*A61B 18/18* (2006.01)

(52) U.S. Cl.
CPC ............ *A61N 5/0624* (2013.01); *A61B 18/18* (2013.01); *A61N 5/0616* (2013.01);
(Continued)

(58) Field of Classification Search
None
See application file for complete search history.

(56) References Cited

U.S. PATENT DOCUMENTS 1,856,969 A * 5/1932 Dionys .................... A61N 5/06
252/582
4,254,339 A * 3/1981 Urano .................. G01N 21/643
250/459.1
(Continued)

FOREIGN PATENT DOCUMENTS

EP    1469290 A1    10/2004
JP    63-501622     6/1988
(Continued)

OTHER PUBLICATIONS

Acton Optics, Optics and Coatings 120 nm-1064 nm, 2008.*
(Continued)

*Primary Examiner* — Carl H Layno
*Assistant Examiner* — Manolis Pahakis
(74) *Attorney, Agent, or Firm* — Hunton Andrews Kurth LLP

(57) ABSTRACT

Certain exemplary embodiments of the present disclosure can provide an apparatus and method for generating at least one radiation can be provided. The exemplary apparatus and/or method can selectively kill and/or affect at least one bacteria. For example, a radiation source first arrangement can be provided which is configured to generate at least one radiation having one or more wavelengths provided in a range of about 190 nanometers (nm) to about 230 nm, and at least one second arrangement can be provided which is configured to prevent the at least one radiation from having any wavelength that is outside of the range can be provided.

11 Claims, 6 Drawing Sheets

Related U.S. Application Data continuation-in-part of application No. PCT/US2012/027963, filed on Mar. 7, 2012.

(60) Provisional application No. 61/450,038, filed on Mar. 7, 2011.

(52) U.S. Cl.
CPC ............... *A61N 2005/0654* (2013.01); *A61N 2005/0661* (2013.01); *A61N 2005/0667* (2013.01)

(56) References Cited

U.S. PATENT DOCUMENTS

| | | | | |
|---|---|---|---|---|
| 4,408,825 | A * | 10/1983 | Stelmack | G02B 5/285 359/360 |
| 4,839,513 | A * | 6/1989 | Wijtsma | A61N 5/06 250/504 R |
| 4,909,254 | A * | 3/1990 | Wilkinson | A61N 5/06 359/359 |
| 4,950,456 | A * | 8/1990 | Forster | G01N 31/12 261/76 |
| 5,776,174 | A * | 7/1998 | Van Tassel | A61N 5/0601 606/15 |
| 5,871,522 | A * | 2/1999 | Sentilles | A61G 13/108 607/88 |
| 6,264,802 | B1 * | 7/2001 | Kamrukov | A61L 2/10 204/157.15 |
| 6,376,972 | B1 | 4/2002 | Tarasenko et al. | |
| 6,730,113 | B2 * | 5/2004 | Eckhardt | A61L 2/10 128/898 |
| 7,201,767 | B2 * | 4/2007 | Bhullar | A61B 1/00165 607/88 |
| 7,381,973 | B2 | 6/2008 | Olstowski | |
| 7,547,391 | B2 * | 6/2009 | Petrie | A61L 2/0011 210/198.1 |
| 8,067,755 | B2 | 11/2011 | Sakamoto et al. | |
| 8,089,057 | B2 * | 1/2012 | Conrady | A61N 5/06 250/458.1 |
| 8,109,981 | B2 * | 2/2012 | Gertner | A61N 5/0603 606/13 |
| 2001/0041935 | A1 | 11/2001 | Valyunin et al. | |
| 2002/0063954 | A1 | 5/2002 | Horton, III | |
| 2003/0015669 | A1 | 1/2003 | Janos et al. | |
| 2003/0018373 | A1 | 1/2003 | Eckhardt et al. | |
| 2003/0023284 | A1 * | 1/2003 | Gartstein | A61L 2/0011 607/88 |
| 2003/0051990 | A1 * | 3/2003 | Spielman | B01D 53/002 204/158.2 |
| 2003/0130709 | A1 * | 7/2003 | D.C. | A61N 5/0619 607/88 |
| 2003/0191459 | A1 * | 10/2003 | Ganz | A61B 18/24 606/15 |
| 2004/0049249 | A1 | 3/2004 | Rubery et al. | |
| 2004/0124367 | A1 | 7/2004 | Olstowski | |
| 2004/0158300 | A1 * | 8/2004 | Gardiner | A61N 5/0619 607/88 |
| 2005/0019256 | A1 * | 1/2005 | Dobkine | A61C 1/0046 424/9.1 |
| 2005/0079096 | A1 | 4/2005 | Brown-Skrobot et al. | |
| 2005/0256554 | A1 * | 11/2005 | Malak | A61N 5/0616 607/88 |
| 2006/0004425 | A1 * | 1/2006 | Cumbie | A61L 2/10 607/86 |
| 2006/0261291 | A1 * | 11/2006 | Gardner, III | A01K 63/06 250/504 R |
| 2007/0103680 | A1 * | 5/2007 | De Vandiere | G01J 3/02 356/301 |
| 2007/0135872 | A1 | 6/2007 | Sumitomo et al. | |
| 2007/0135874 | A1 | 6/2007 | Bala | |
| 2007/0189018 | A1 | 8/2007 | Tausch et al. | |
| 2007/0219600 | A1 * | 9/2007 | Gertner | A61N 5/0603 607/88 |
| 2007/0255266 | A1 | 11/2007 | Cumbie et al. | |
| 2007/0276455 | A1 * | 11/2007 | Fiset | A61C 19/066 607/91 |
| 2008/0067418 | A1 | 3/2008 | Ross | |
| 2008/0096097 | A1 | 4/2008 | Singh | |
| 2009/0036953 | A1 | 2/2009 | Gustavsson | |
| 2009/0093865 | A1 * | 4/2009 | Krespi | A61N 5/0603 607/88 |
| 2009/0131922 | A1 * | 5/2009 | Dewey | A61B 18/203 606/9 |
| 2009/0143842 | A1 * | 6/2009 | Cumbie | A61N 5/0616 607/88 |
| 2009/0171326 | A1 * | 7/2009 | Hohla | A61F 9/00736 606/6 |
| 2010/0007492 | A1 | 1/2010 | Ressler et al. | |
| 2010/0028201 | A1 | 2/2010 | Neister | |
| 2010/0222852 | A1 * | 9/2010 | Vasily | A61N 5/0603 607/89 |
| 2010/0320405 | A1 * | 12/2010 | Gardner, III | G01J 3/10 250/504 H |
| 2011/0054574 | A1 | 3/2011 | Felix | |
| 2012/0172950 | A1 | 7/2012 | Choi et al. | |
| 2012/0313532 | A1 | 12/2012 | Stibich et al. | |
| 2013/0085385 | A1 | 4/2013 | Luiken | |
| 2013/0209940 | A1 * | 8/2013 | Sakamoto | C08G 8/08 430/319 |
| 2014/0116961 | A1 * | 5/2014 | Bokermann | C02F 1/008 210/748.11 |
| 2015/0073396 | A1 | 3/2015 | Randers-Pehrson et al. | |
| 2015/0308962 | A1 * | 10/2015 | Mazzillo | G01N 21/85 250/208.2 |
| 2017/0290932 | A1 * | 10/2017 | Mori | A61N 5/06 |

FOREIGN PATENT DOCUMENTS

| | | |
|---|---|---|
| JP | 2007-159785 | 6/2007 |
| JP | 2007-524801 | 8/2007 |
| WO | WO 87/02256 | 4/1987 |
| WO | WO 2004/061415 A2 | 7/2004 |
| WO | 2012122210 A1 | 9/2012 |

OTHER PUBLICATIONS

Hamin Jeon, Assessment of UV Excilamps for Wound Sterilization, RARAF, Columbia University, Aug. 5, 2011 (retrieved from the Wayback Machine with address http://www.nevis.columbia.edu/reu/2011/JeonReport.pdf, dated Dec. 12, 2011 ).*
Newport, Custom Bandpass Filter Capability, 2009 (retrieved from the Wayback Machine with address http://www.newport.com/Custom-Bandpass-Filter-Capability/372584/1033/catalog.aspx, dated Mar. 9, 2009).*
Japanese Office Action Application No. 2013-557814 dated Jan. 5, 2016.
User Manual for KrCl-excilamps (BD_P models) pp. 1-6; Oct. 1, 2010.
E. Sosnin and T. Oppenlander "Applications of capacitive and barrier discharge excilamps in photoscience" J Photochemistry and Photobiology vol. 7 pp. 145-163 (2006).
Barie PS et al. "Surgical site infections." Surg Clin North Am.,•85 (6): pp. 1115-1135 (2005).
Hart D. "Bactericidal ultraviolet radiation in the operating room. Twenty-nine-year study for control of infections." J. Am. Med Assoc., 172: (10) pp. 1019-1028 (1960).
Mitchell DL et al. "The biology of the (6-4) photoproduct" Photochemistry and Photobiology, 49(6) pp. 805-819 (1989).
Witkin EM, "Ultraviolet mutagenesis and inducible DNA repair in *Escherichia coli*" Bacteriological Review, 40(4) pp. 869-907 (1976).
Koch-Paiz CA et al. "Functional genomics of UV radiation responses in human cells" Mutation Research, 549 pp. 65-78 (2004).
Lorents DC. "A model of rare-gas excimer formation and decay and its application to vuv lasers" Radiation Research 59(2) pp. 438-440 (1974).
Measures RM, "Prospects for developing a laser based on electrochemiluminescence" Applied Optics, 13(5) pp. 1121-1133 (1974).

(56) References Cited

OTHER PUBLICATIONS

Pallikaris IG et al. "Laser in situ keratomileusis" Lasers in Surgery and Medicine 10(5) pp. 463-468 (1990).
Sosnin EA et al. "Applications of capacitive and barrier discharge excilamps in photoscience" J Photochem. Photobiol C: Photochem. Rev. 7 pp. 145-163 (2006).
Sosnin EA et al. "A bacterial barrier-discharge KrBr Excilamp" Instr. Experiment. Tech. 48, pp. 663-666 (2005).
Matafonova GG et al. Efficiency of KrCl excilamp (222 nm) for inactivation of bacteria in suspension. Lett Appl Microbio 47(6) pp. 508-513 (2008).
Wang D et al. "Comparison of the disinfection effects of vacuum-UV (VUV) and UV light on Bacillus subtilis . . . 172, 222 and 254 nm." Photochem Photobiol 86(1) pp. 176-181(2010).
Belyakov OV et al. "Biological effects in unirradiated human tissue induced by radiation damage up to 1 mm away" Proc. Natl. Acad. Sci. 102 (40) pp. 14203-14208 (2005).
Su Y et al. "Analysis of ionizing radiation-induced DNA damage and repair in threedimensional human skin model system" Exp Dermatol 19(8):e16-22, (2010).
Giannini GT et al. "Infected wound model development of an in vitro . . . activity and antimicrobial treatment through Microdialysis" Adv Skin Wound Care 23(8) pp. 358-364 (2010).
Mc Loughlin RM et al. "CD4+ T cells and CXC chemokines modulate the pathogenesis of *Staphylococcus aureus* wound infections" Proc. Natl. Acad Sci.103(27) pp. 10408-10413(2006).
Kvam E et al. "Induction of oxidative DNA base damage in human skin cells by UV and near visible radiation" Carcinogenesis 18(12) pp. 2379-2384 (1997).
Pattison DI, Davies MJ "Actions of ultraviolet light on cellular structures" Cancer: Cell Structures, Carcinogen and Genomic Instability 96 pp. 31-57 (2006).
Conner-Kerr TA et al. "The effects of ultraviolet radiation on antibiotic-resistant bacteria in vitro" Ostomy Wound Manage. 44(10) pp. 50-56 (1998).
Green H et al. "Cytotoxicity and mutagenicity oflow intensity, 248 and 193 nm excimer laser radiation in mammalian cells" Cancer Research 47 pp. 410-413 (1987).
McDonald RS et al. 405nm Light exposure of osteoblasts and inactivation of bacterial isolates from arthroplasty patients: . . . applications? Eur Cell Mater 25 pp. 204-214 (2013).
Dai T etal. "Ultraviolet C irradiation: an alternative antimicrobial approach to localized infections?" Expert Rev Anti Infect Ther 10 (2) pp. 185-195 (2012).
Papadopoulo D et al "Hypomutability in Fanconi anemia cells is associated with increased deletion frequency at the HPRT locus" Proc Nat/ Acad Sci. 87 pp. 8383-8387 (1990).
Zolzer F et al, Wavelength dependence of inactivation and mutation induction to 6-thioguanine-resistance in . . . fibroblasts. Photochem Photobiol 40 pp. 50-53 (1984).
Lidwell OM, et al. "Airborne contamination of wounds injoint replacement operations: the relationship to sepsis rates." J Hosp Infect 4 pp. 111-131; (1983).
Gosden PE et al. "Importance of air quality and related factors in the prevention of infection in orthopaedic implant surgery" Journal Hospital Infection 39 pp. 173-180 (1998).
Ritter MA et al "Ultraviolet lighting during orthopaedic surgery and the rate of infection" Journal of Bone and Joint Surgery 89 pp. 1935-1940 (2007).
Stock GW et al. "Directed air flow to reduce airborne particulate and bacterial contamination . . . field during total hip arthroplasty" Jou of Arthroplasty 26 pp. 771-776 (2011).
Frei E et al. "Microbial pathogenesis of bacterial biofilms: a causative factor of vascular surgical site infection" Vasc Endovascular Surg 45 pp. 688-696 (2011).
Milller J et al. "Development of a fiber-optic delivery system capable of delivering 213 and 266 nm pulsed Nd: YAG . . . fluid environment" Applied Optics 50 pp. 876-885 (2011).
Salvermoser M, Murnick DE "High-efficiency, high-power, stable 172 nm xenon excimer light source" Applied Physics Letter 83(10) pp. 1932-1934 (2003).
Hitzschke L et al "Product families . . . discharges" In: Bergman RS, editor. Proc of the 9th Int'l Symp on the Sci & Tech of Light Sources, Cornell Univ Press pp. 411-421(2001).
Reed NG "The history of ultraviolet germicidal irradiation for air disinfection" Public Health Reports 125 pp. 15-27 ( 2010).
Nardell EA et al. "Safety of upper-room ultraviolet germicidal . . . room occupants: results from the Tuberculosis Ultraviolet Shelter Study" Publ Health Rep 123 pp. 52-60 (2008).
Escombe et al. Upper-room ultraviolet light and negative air ionization to prevent tuberculosis transmission. PLoS Med 6, e43 pp. 1-11 (2009).
Wengraitis S et al Ultraviolet spectral reflectance of ceiling tiles, and implication . . . ultraviolet germicidal irradiation. Photochem Photobiol 88 pp. 1480-1488 (2012).
Sliney D "Balancing the risk of eye irritation from UV-C with infection from bioaerosols" Photochem Photobio 89 pp. 770-776 (2013).
Sosnin EA et al "Applications of capacitive and barrier discharge . . . photoscience" J of Photochemistry . . . , Elsevier, Amsterdam, NL, vol. 7, No. 4, (2006), p. 145-163.
G.G. Matafonova et al "Efficiency of KrCl excilamp (222?nm) for inactivation of bacteria in suspension", Letters in Applied Microbiology, vol. 47, No. 6, (2008), p. 508-513.
European supplemental Search Report for European Application No. 12755325.3 dated Jul. 15, 2014.
International Search Report for International Patent Application No. PCT/US2012/027963 dated Jul. 11, 2012.
International Written Opinion for International Patent Application No. PCT/US2012/027963 dated Jul. 11, 2012.
Oppenlander et al. "Mercury-free Vacuum-(VUV) and UV Excilamps: Lamps of the Future?" I UVA News; vol. 7, No. 4; pp. 16-20 (Dec. 2005).
Newport, Custom Bandpass Filter Capability, 2009 (retrieved from the Wayback Machine w/ address http://www.newport.com/Custom-Bandpass-Filter-Capability/372584/1033/catalog.as.
Hamin Jeon, Assessment of UV Excilamps for Wound Sterilization, RARAF, CU, Aug. 5, 2011 (retrieved from theWayback Machine with address http://www.nevis.columbia.edu/reu/2011/Jeon.
Hargrave's Communications Dictionary, Interference Filter, Wiley, 2001.
Buonanno et al., 207-nm UV Light—A Promising Tool for Safe Low-Cost Reduction of Surgical Site Infections. 1: In Vitro Studies, PLoS One, vol. 8:10, Oct. 2013.
Lomaev et al., Capacitive & Barrier Discharge Excilamps &Their Applications (Review), Instruments and Experimental Techniques, 2006, vol. 49, No. 5, pp. 595-616, Pleiades.
Sosnin et al., Capacitive Discharge Excilamps, Laser Applications in Microelectronic and Optoelectronic Manufacturing V, Proceedings of SPIE vol. 3933 (2000).
International Search Report and Written Opinion dated Sep. 2, 2016 for International Application No. PCT/US16/35680.
McDevitt, James J. et al., "Characterization of UVC Light Sensitivity of Vaccine Virus", Applied & Environmental Microbiology, vol. 73, No. 18, Sep. 2007, pp. 5760-5766.
Tscherteu et al., KPN Tower, Rotterdamn, Aarhus, Denmark, Media Architecture Institute Vienna/Sydney and Aarhus University, 2000 and 2012.
Sosnin et al., "Capacitive Discharge Excipled Lamps," J. Phys. D: Appl. Phys. 38, pp. 3194-3201, 2005.
Panchenko et al., "Planar Excilamp on Rare Gas Chlorides pumped by a Transverse Self-Sustained Discharge," Quantum Electronics, vol. 36, No. 2, pp. 169-173.
Mizunami et al., "Buffer Gas Effect in a Discharge-Pumped XeBr Excimer Laser," Journal of Applied Physics, vol. 71, p. 2036, 1992.
Lomaev et al., "Vacuum-ultaviolet Excilamps with Excitation by a Barrier Corona Discharge," J. Opt. Technol., vol. 79, No. 8, Aug. 2012.
Sosnin et al., "Bacterial Iodine Lamp Excited by Capacitive Discharge," Technical Physics Letters, vol. 30, No. 7, pp. 615-617, 2004.

(56) References Cited

OTHER PUBLICATIONS

The Chambers Dictionary, definition of "any", 2015.
Japanese language Notice of Allowance for 2013-557814, 2016.
Japanese language Notice of Allowance for 2016-127873, 2018.
Harm, Walter, "Biological Effects of Ultraviolet Radiation," Cambridge, UK: Cambridge University Press, pp. 1-216, 1980.
Extended European Search Report dated May 17, 2018 from European patent application No. 16804508.6.
Notice of Allowance for Japanese Patent Application No. 2013-557814 dated Sep. 26, 2016.
Allowed claims, in English for Japanese Patent Application No. 2013-557814.
Notice of Allowance for Japanese Patent Application No. 2016-127873 dated Feb. 7, 2018.
Notice of Reasons for Rejection dated Apr. 18, 2017 for Japanese National Phase Application No. 2016-127873.
Communication pursuant to Article 94(3) EPC dated Feb. 18, 2019 for European Patent Application No. 12755325.3.

\* cited by examiner

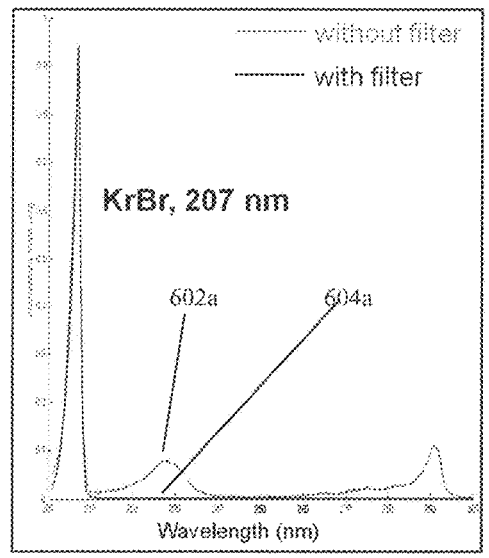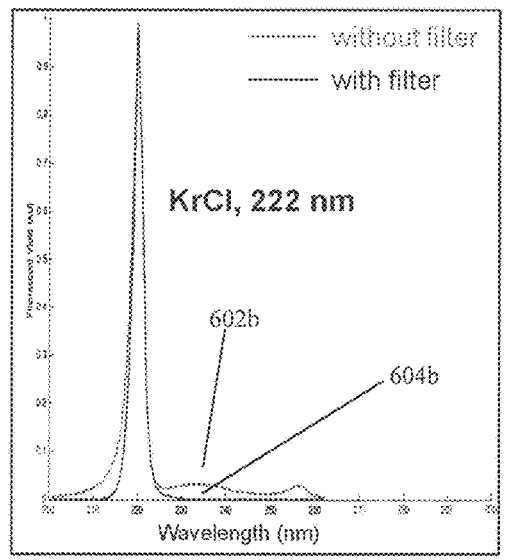
Figure 6A          Figure 6B
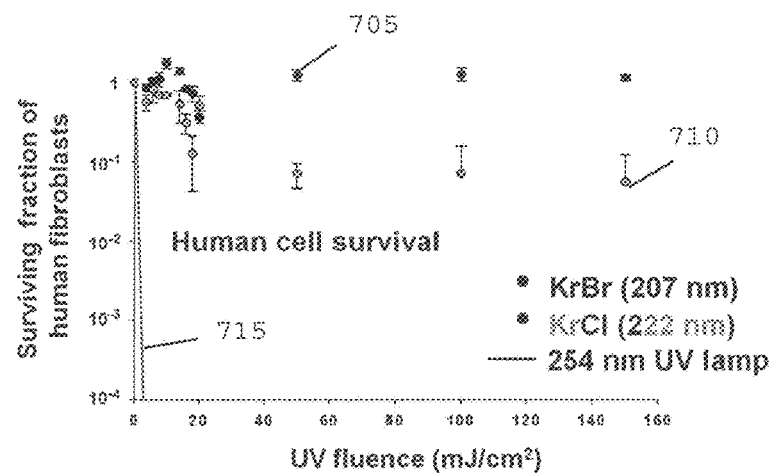
Figure 7

APPARATUS, METHOD, AND SYSTEM FOR SELECTIVELY EFFECTING AND/OR KILLING BACTERIA

CROSS-REFERENCE TO PRIOR APPLICATION(S)

This present application is a divisional application and claims priority to U.S. patent application Ser. No. 14/021,631, filed on Sep. 9, 2013, which was issued as U.S. Pat. No. 10,071,262 on Sep. 11, 2018, which claims the benefit and priority from U.S. Provisional Application Ser. No. 61/450,038, filed on Mar. 7, 2011, and International Application No. PCT/US2012/027963, filed on Mar. 7, 2012, the disclosures of which are incorporated by reference herein in their entireties.

FIELD OF THE DISCLOSURE

Exemplary embodiments of the present disclosure relate to selectively affecting and/or killing bacteria, and more specifically to exemplary apparatus, methods and systems which can use an ultraviolet radiation to selectively affecting and/or killing bacteria while not harming human cells.

BACKGROUND INFORMATION

It has been estimated that between 2% and 5% of clean surgeries result in surgical site infections (SSI). Patients who develop SSI can be 60% more likely to spend time in an ICU, can be 5 times as likely to be readmitted, can have a mortality rate twice that of noninfected patients, can have an average of 7 days additional length of hospital stay, and can have an average of about $3,000 additional costs. It has been estimated that about 40-60% of SSIs can be preventable (see, e.g., Barie P S, Eachempati S R. *Surgical site infections. Surg Clin North Am* 2005; 85(6):1115-35, viii-ix).

It has been approximately 50 years since Deryl Hart and colleagues at Duke University showed that ultraviolet (UV) irradiation of surgical wounds can be a highly effective methodology for reducing surgical wound infection rates (see, e.g., Hart D. *Bactericidal ultraviolet radiation in the operating room. Twenty-nine-year study for control of infections. J Am Med Assoc* 1960; 172:1019-28). However, UV radiation can be a hazard both to the patient and to the operating team, and the use of additional clothing, hoods, and eye shields for protection can be both cumbersome and costly, preventing widespread use of the technique.

UV radiation can be a very efficient bactericidal agent, and the mechanisms by which it mutates and kills bacteria, as well as human cells, are well established (see, e.g., Mitchell D L, Nairn R S. *The biology of the (6-4) photoproduct. Photochem Photobiol* 1989; 49(6):805-19; Witkin E M. *Ultraviolet mutagenesis and inducible DNA repair in Escherichia coli. Bacteriol Rev* 1976; 40(4):869-907; Koch-Paiz C A, Amundson S A, Bittner M L, Meltzer P S, Fornace A J, Jr. *Functional genomics of UV radiation responses in human cells. Mutat. Res.* 2004; 549(1-2):65-78; and Harm W. *Biological effects of ultraviolet radiation.* Cambridge, UK: Cambridge University Press, 1980). Ultraviolet germicidal irradiation (UVGI) has been used to break down microorganisms in food, air, and water purification. UVGI typically uses a short wavelength of UV, typically in the UVB or UVC range, to destroy nucleic acids in small organisms, removing their reproductive capabilities. UV irradiation (including UVGI) is typically produced with low-pressure mercury lamps, which can produce a range of UV wavelengths, ranging from UVA (wavelengths 400 to 320 nm) to UVB (wavelengths 320 to 290 nm) to UVC (wavelengths 290 to 100 nm). FIG. 1 shows the spectrum of UV wavelengths emitted from a typical mercury UV lamp. UVGI is typically produced by mercury-vapor lamps that emit at around 254 nm. However, UVGI lamps may be harmful to humans and other life forms, and are typically shielded or in environments where exposure is limited.

UV lamps can also facilitate a UV emission from an excited molecule complex (e.g., an exciplex, such as either krypton-bromine or krypton-chlorine), using arrangements called excilamps. The basic theory behind exciplex UV emission was developed in the 1970s (see, e.g., Lorents D C. *A model of rare-gas excimer formation and decay and its application to vuv lasers. Radiat. Res.* 1974; 59(2):438-40; and Measures R M. *Prospects for developing a laser based on electrochemiluminescence. Appl Opt* 1974; 13(5):1121-33). The first excimer lasers were made in the 1980s and they are now in common use, for example, e.g., in LASIK opthalmic surgery (see, e.g., Pallikaris I G, Papatzanaki M E, Stathi E Z, Frenschock O, Georgiadis A. *Laser in situ keratomileusis. Lasers Surg Med* 1990; 10(5):463-8). Current excimer lasers, however, are typically not feasible for wound sterilization both in terms of beam size (e.g., excimer laser beams are very narrow) and their high cost. In the past, an excimer lamp (excilamp) has been developed in Russia (see, e.g., Sosnin E A, Oppenlander T, Tarasenko V F. *Applications of capacitive and barrier discharge excilamps in photoscience. J. Photochem. Photobiol C: Photochem. Rev.* 2006; 7:145-63), which can produce a wide high-intensity beam of single-wavelength UV radiation. These lamps can be small, inexpensive (e.g., ~$1,000), high powered (e.g., wound irradiation time can be a few seconds), and long-lived (e.g., 1,000 to 10,000 hours). Certain papers (see, e.g., Sosnin E A, Avdeev S M, Kuznetzova E A, Lavrent'eva L V. *A bacterial barrier-discharge KrBr Excilamp. Instr. Experiment. Tech.* 2005; 48:663-66; Matafonova G G, Batoev V B, Astakhova S A, Gomez M, Christofi N. *Efficiency of KrCl excilamp (222 nm) for inactivation of bacteria in suspension. Lett Appl Microbiol* 2008; 47(6):508-13; and Wang D, Oppenlander T, El-Din M G, Bolton J R. *Comparison of the disinfection effects of vacuum-UV (VUV) and UV light on Bacillus subtilis spores in aqueous suspensions at 172, 222 and 254 nm. Photochem Photobiol* 2010; 86(1):176-81) have been published on their bactericidal properties (as expected they are highly efficient), but the concept that these lamps will kill bacteria but not human cells is not described.

Thus, there may be a need to address at least some of the deficiencies and/or issues that to date remained with respect to the above-described conventional systems and methods.

SUMMARY OF EXEMPLARY EMBODIMENTS

Accordingly, exemplary embodiments of the apparatus, methods and systems can be provided that can address at least some of such deficiencies. For example, the exemplary embodiments of the apparatus, methods and systems can use an ultraviolet radiation to selectively affecting and/or killing bacteria while not harming human cells.

In particular, in certain exemplary embodiments of the present disclosure, a UV irradiator, e.g., the excilamp, can be provided which can effect and/or kill bacteria, without being harmful to human cells. The exemplary system, method and apparatus takes into consideration that bacteria are typically physically much smaller than human cells, and thus, an appropriately chosen UV wavelength (e.g., around 207 nm to 220 nm) preferably penetrates and kills bacteria, but preferably would not be able to penetrate into the biologically sensitive nucleus of human cells. Irradiating a wound with this exemplary tailored UV radiation, for example, can therefore provide the advantages of UV bacteriological sterilization, while being safe for patient and staff, and preferably not requiring protective clothing/hoods/eye shields, or the like. According to another exemplary embodiment of the present disclosure, the room air (as opposed to the wound), or surfaces (e.g., walls, floors, ceiling, countertops, furniture, fixtures, etc.) can be exposed to this exemplary UV lamp in hospital environments.

According to further exemplary embodiments of the present disclosure, it is possible to provide exemplary UV lamps that can emit at a single wavelength, in contrast to standard mercury UV lamps which typically emit over a wide range of wavelengths. The exemplary lamps can include UV emitted from an excited molecule complex (e.g., an exciplex, such as either krypton-bromine or krypton-chlorine), called excilamps, and can be modified in accordance with certain exemplary embodiments of the present disclosure to produce UV having a single wavelength, thus, facilitating modifying the UV irradiation to have enough energy to penetrate and kill bacteria, but not enough range to penetrate to the nucleus of human cells. This can be performed based on certain exemplary embodiments, e.g., using one or more modulators, wavelength-effecting masks, etc.

Certain exemplary embodiments of the present disclosure can be tested, for example, in an in-vitro (laboratory) human skin system (see, e.g., Belyakov O V, Mitchell S A, Parikh D, Randers-Pehrson G, Marino S, Amundson S A, et al. *Biological effects in unirradiated human tissue induced by radiation damage up to 1 mm away. Proc. Natl. Acad. Sci. U.S.A.* 2005; 102:14203-08; and Su Y, Meador J A, Geard C R, Balajee A S. *Analysis of ionizing radiation-induced DNA damage and repair in three dimensional human skin model system. Exp Dermatol* 2010; 19(8):e16-22), in an in-vitro wound infection model (see, e.g., Giannini G T, Boothby J T, Sabelman E E. *Infected wound model development of an in vitro biomaterial-protected wound infection model to study microbial activity and antimicrobial treatment through microdialysis. Adv Skin Wound Care* 2010; 23(8):358-64), in a clinically relevant mouse model of surgical wound infection (see, e.g., McLoughlin R M, Solinga R M Rich J, Zaleski K J, Cocchiaro J L, Risley A, et al. *CD4+ T cells and CXC chemokines modulate the pathogenesis of Staphylococcus aureus wound infections. Proc. Natl. Acad. Sci. U.S.A.* 2006; 103(27):10408-13), in a nude mouse model for in-vivo safety standards, in large animal studies, or in studies in the clinic. The exemplary excilamp wound irradiation can facilitate a practical and inexpensive approach to significantly reducing surgical site infections.

According to certain exemplary embodiments of the present disclosure, a UV radiation at approximately 207 nm to 220 nm can be provided, for example, that can differentially damage and/or kill methicillin-resistant *Staphylococcus aureus* (MRSA), relative to human cells. Although a conventional germicidal UV lamp can be approximately equally efficient at killing MRSA and human cells, by contrast, the exemplary 207 to 220 nm wavelength UV from excilamps can be approximately 5,000 times more efficient at killing MRSA relative to human cells.

According to certain exemplary embodiments of the present disclosure, apparatus and method for generating at least one radiation can be provided. According to certain exemplary embodiments, the exemplary apparatus and/or method can selectively kill and/or affect at least one bacteria. For example, a radiation source first arrangement configured to generate at least one radiation having one or more wavelengths provided in a range of about 190 nanometers (nm) to about 230 nm, and at least one second arrangement configured to substantially prevent the at least one radiation from having any wavelength that is outside of the range can be provided. The radiation can be configured to selectively affect or destroy at least one bacteria on or within a body, while substantially avoiding harm to cells of the body. The radiation source can include a krypton-bromine lamp or a krypton-chlorine lamp excilamp. Additionally, the radiation source first arrangement can be further configured to generate the at least one radiation having a single wavelength provided in the range, and the at least one second arrangement can be further configured to prevent the radiation from having any wavelength other than the single wavelength. The single wavelength can be about 207 nm, and/or about 222 nm. Further, the second arrangement can include at least one of a chemical filter or a dielectric.

According to yet another exemplary embodiment, systems and methods can be provided for generating at least one radiation. For example, e.g., using a radiation source first arrangement or another arrangement, it is possible to generate the radiation(s) having one or more wavelengths provided in a range of about 190 nanometers (nm) to about 230 nm. Further, it is possible to, using at least one second arrangement and/or the same arrangement, to substantially prevent the radiation(s) from having any wavelength that is outside of the range.

The radiation(s) can be configured to selectively affect or destroy at least one bacteria on or within a body, while substantially avoiding harming to any of cells of the body. The radiation source can include an excilamp, a krypton-bromine lamp and/or a krypton-chlorine lamp. The radiation source first arrangement can be further configured to generate the radiation(s) having a single wavelength provided in the range, and the second arrangement(s) can be further configured to prevent the radiation(s) from having any wavelength other than the single wavelength. The single wavelength can be about 206 nm, 207 nm, and/or 222 nm. The second arrangement can include a chemical filter and/or a dielectric.

These and other objects, features and advantages of the present disclosure will become apparent upon reading the following detailed description of embodiments of the present disclosure in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIGS. 6(a) and 6(b) are spectral graphs of exemplary excilamps according to certain exemplary embodiments of the present disclosure;

FIG. 7 is a graph of human cell survival with respect to ultra violet fluence, according to certain exemplary embodiments of the present disclosure;

Figure 1:
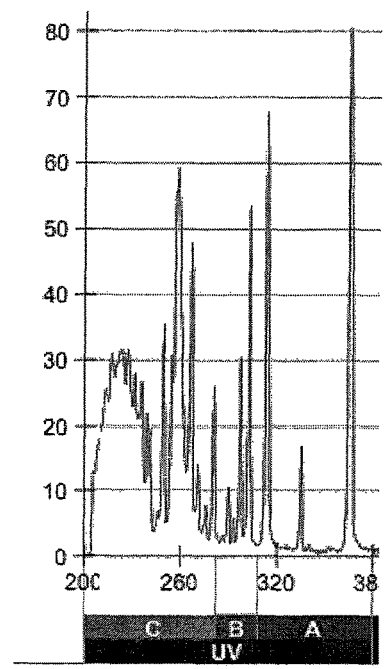
FIG. 1 is a graph of an exemplary spectrum of UV wavelengths generated by a typical mercury UV lamp.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures and the accompanying claims.

DETAILED DESCRIPTION OF EXEMPLARY EMBODIMENTS

UV radiations of different wavelengths can have different abilities to penetrate into cells. Typically, the higher the wavelength, the more penetrating the radiation, and the lower the wavelength, the less penetrating the radiation. For example, UV radiation with a low wavelength of about 200 nm, for example, while able to pass through water quite efficiently, can be heavily absorbed in the outer part of a human cell (the cytoplasm, see, for example, FIG. 2), and may not have enough energy to reach the biologically sensitive cell nucleus.

Figure 2:
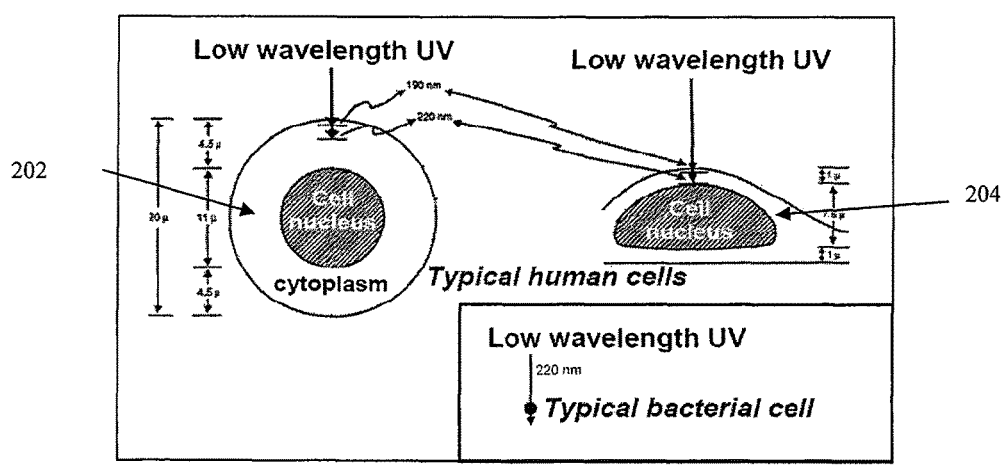
FIG. 2 is an illustration of an exemplary penetration of low wavelength UV radiation with respect to human cells and bacteria in accordance with an exemplary embodiment of the present disclosure.

The limited penetrating ability of ~200 nm UV radiation can be used, as shown in FIG. 2, because bacteria are typically physically far smaller than human cells. Specifically, a typical bacterial cell is less than about 1 μm (micrometer) in diameter, whereas human cells are typically about 10 to 30 μm across, depending on their type and location.

In particular, FIG. 2 shows a typical human cell nucleus having a spherical geometry 202 or a flattened geometry 204, illustrating the penetration into a human cell of UV radiation with wavelength of around 200 nm. As shown in FIG. 2, essentially no UV of this wavelength preferably reaches the cell nucleus 202, 204, which contains the radiation-sensitive DNA. Accordingly, UV radiation of this wavelength would typically not be harmful to human cells or thus to humans. In addition to this geometric reason, there can be a biological reason why UV with a wavelength around 200 nm UV will typically not be harmful to humans. At about 185 nm and below, UV can be very efficiently absorbed by oxygen, producing ozone and oxidative damage. Above about 240 nm, UV can be very efficient at producing oxidative DNA base damage (see, e.g., Kvam E, Tyrrell R M *Induction of oxidative DNA base damage in human skin cells by UV and near visible radiation. Carcinogenesis* 1997; 18(12):2379-84; and Pattison D I, Davies M J. *Actions of ultraviolet light on cellular structures. EXS* 2006(96):131-57). Thus, 200 nm wavelength UV can be in a narrow UV "safety window". In contrast, because bacteria are typically physically much smaller in size than human cells, UV radiation with wavelength around 200 nm can penetrate through, and therefore kill, bacteria.

According to exemplary embodiments of the present disclosure, it is possible to utilize one or more UV excilamps which, in contrast to standard UV lamps, can produce UV radiation at a specific wavelength—e.g., around 200 nm. UV radiation around such exemplary wavelength (e.g., a single wavelength or in a range of certain wavelengths as described herein) can penetrate and kill bacteria, but preferably would not penetrate into the nucleus of human cells, and thus, can be expected to be safe for both patient and staff.

Exemplary Excilamp UV Irradiator

Figure 3:
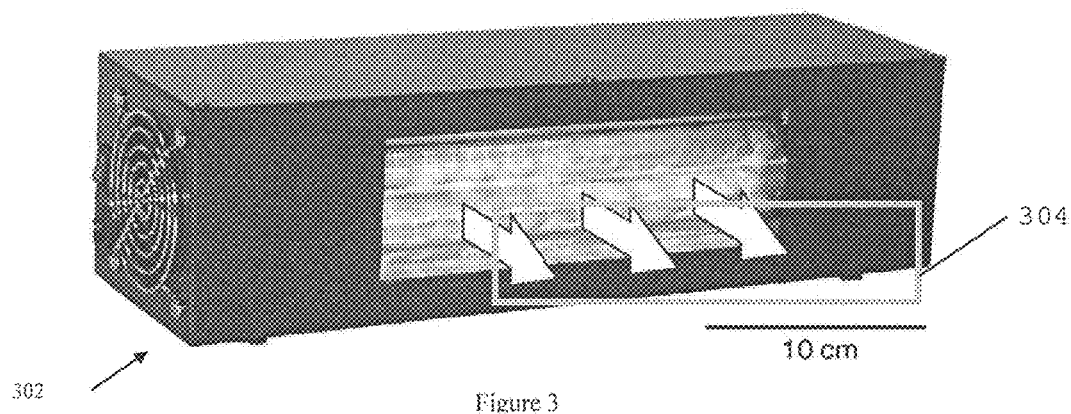
FIG. 3 is an illustration of an exemplary excilamp which can provide the UV radiation with at a single wavelength or in a particular range of wavelengths in accordance with an exemplary embodiment of the present disclosure.
Figure 4:
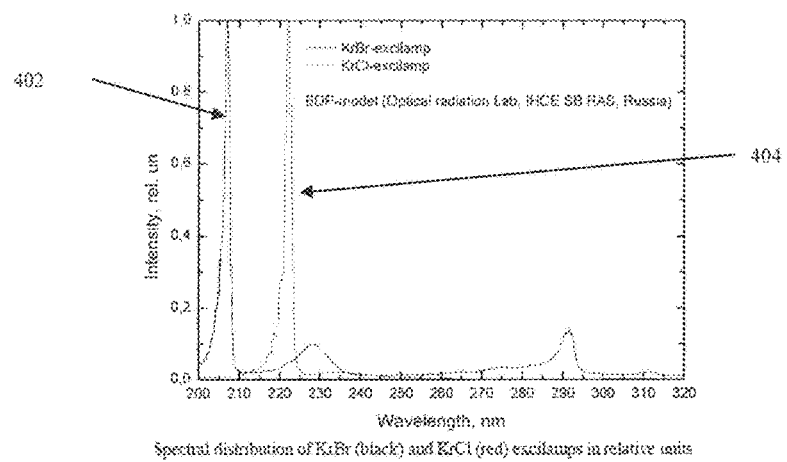
FIG. 4 is a graph of the exemplary spectral distributions of the UV radiation generated by excilamps in accordance with certain exemplary embodiments of the present disclosure.

The exemplary excilamp technology can utilize certain exemplary concepts which were developed at the Institute of High Current Electronics (IHCE) in Tomsk, Siberia (see, e.g., Sosnin E A, Oppenlander T, Tarasenko V F. *Applications of capacitive and barrier discharge excilamps in photoscience. J. Photochem. Photobiol C: Photochem. Rev.* 2006; 7:145-63.). Additional exemplary excilamps that can be utilized with the exemplary embodiments of the present disclosure may be available from Heraeus Noblelight in Germany. The IHCE lamps, an exemplary embodiment of such lamp 302 is shown in FIG. 3, can be small, rugged, cost ~$1,000, and can be made to produce a variety of single wavelength UV radiations. Based on the considerations above, exemplary embodiments of the present disclosure can use, for example, a krypton-bromine lamp excilamp, which can produce UV at about 207 nm, or a krypton-chlorine lamp (FIG. 3), which can produce UV at about 222 nm. Another exemplary excilamp can produce UV at about 206 nm. The exemplary spectrum of these lamps are shown in the graph of FIG. 4. As shown in FIG. 4, a spectral distribution 402 can be produced by a krypton-bromine lamp, and spectral distribution 404 was produced by a krypton-chlorine lamp. Additionally, according to further exemplary embodiments of the present disclosure, certain exemplary features can be a filter 304 (e.g., spectrum filtering elements such as multilayer dielectric filters or chemical filters) to remove unwanted wavelengths, or those wavelengths that are outside of the preferable range of wavelengths. For example, absorption and/or reflective elements can be provided between the lamp and the irradiated surface to filter unwanted wavelengths, such as, e.g., a band-pass filter, a long-wavelength blocking filter. In one exemplary embodiment, the absorptive material can be fluorescent, such that it emits visible light when it absorbs UV radiation to provide an indication that the lamp is operating. Alternatively or in addition, other gases can be added to the lamp to suppress unwanted wavelengths. For example, adding argon to the krypton-chlorine lamp can suppress generation of the 228 nm UV.

The typical power output of the air-cooled excilamps can be about 7.5 to 20 mW/cm$^2$, although higher power can be obtained in a water-cooled system. At about 20 mW/cm$^2$, only a few seconds of exposure can deliver about 20 mJ/cm$^2$, which can be a typical bactericidal dose.

Exemplary embodiments of the present disclosure can provide an excilamp, emitting about a 207 nm or about a 222 nm single wavelength UV radiation, to differentially kill bacteria while sparing adjacent human cells. Further, the wavelength(s) of the UV radiation according to further exemplary embodiments of the present disclosure can be in the range of about 190 nanometers (nm) to about 230 nm. Exemplary experiments implementing embodiments of the present disclosure can include: an in-vitro (laboratory) 3-D human skin system (see, e.g., Belyakov O V, Mitchell S A, Parikh D, Randers-Pehrson G, Marino S, Amundson S A, et al. *Biological effects in unirradiated human tissue induced by radiation damage up to* 1 *mm away. Proc. Natl. Acad. Sci. U.S.A.* 2005; 102:14203-08; and Su Y, Meador J A, Geard C R, Balajee A S. *Analysis of ionizing radiation-induced DNA damage and repair in threedimensional human skin model system. Exp Dermatol* 2010; 19(8):e16-22); a nude mouse model for in-vivo safety standards; an in-vitro wound infection model (see, e.g., Giannini G T, Boothby J T, Sabelman E E. *Infected wound model development of an in vitro biomaterial-protected wound infection model to study microbial activity and antimicrobial treatment through microdialysis. Adv Skin Wound Care* 2010; 23(8):358-64); a clinically relevant mouse model of surgical wound infection (see, e.g., McLoughlin R M Solinga R M Rich J, Zaleski K J, Cocchiaro J L, Risley A, et al. *CD4+ T cells and CXC chemokines modulate the pathogenesis of Staphylococcus aureus wound infections. Proc. Natl. Acad. Sci. U.S.A.* 2006; 103(27):10408-13); larger animal model studies; studies in a clinic. According to yet another exemplary embodiment of the present disclosure, excilamp irradiation can be provided for a wound, a room air and/or surfaces (e.g., walls, floors, ceiling, countertops, furniture, fixtures, etc.), which can facilitate a practical and inexpensive approach to significantly reducing surgical wound infection.

In an exemplary experiment implementing certain exemplary embodiments of the present disclosure, an exemplary test bench was developed for gathering, e.g., exemplary preliminary sterilization results from exemplary UV light sources. For example, the exemplary test bench can include: a) a light-tight box; b) a shutter control; c) a filter holder; and d) adjustable exposure parameters for time, distance, and wavelength (e.g., 207 nm KrBr excilamp, 222 nm, KrCl excilamp, and 254 nm standard germicidal lamp). Additionally, exemplary custom filters can be designed to eliminate higher-wavelength components in the excilamp emission spectra to provide optimal single-wavelength exposure. A UV spectrometer and deuterium lamp (e.g., for equipment calibration) can be used to validate the filter effectiveness, as shown, for example, in FIGS. 6(*a*) and 6(*b*), which illustrate the normalized spectra comparing excilamp emission (red—602*a* and 602*b*) with filtered excilamp emission (blue—604*a* and 604*b*) for both KrBr and KrCl excilamps. This exemplary test bench facilitated, for example, a generation of biological findings of filtered excilamp exposure to both bacteria and healthy human cells, which are described below. In turn, the exemplary biological testing experience has provided details regarding exemplary parameters for developing filtered KrBr and KrCl excilamps into optimal devices for clinical applications.

Exemplary Biological Results

Described below are certain exemplary experiments implementing certain exemplary embodiments of the present disclosure. The exemplary experiments investigated, for example, whether UV from exemplary filtered excilamps can be effective at killing bacteria while sparing normal human cells.

In the exemplary experiment, human fibroblasts were, for example, exposed to about 3 mJ/cm$^2$ from a standard germicidal UV lamp (e.g., 254 nm), and their survival was less than about $10^{-4}$. By contrast, when they were exposed to fluences as high as 150 mJ/cm$^2$ from the exemplary filtered KrBr or KrCl excilamp (e.g., 207 and 222 nm, respectively), their survival was in the range from about 1 to about $10^{-1}$ (see FIG. 7). Indeed, FIG. 7 shows an exemplary graph indicating a clonogenic survival of normal human skin fibroblasts (AG1522) exposed to UV from exemplary filtered KrBr (207 nm) or KrCl (222 nm) excilamps, or from a conventional germicidal lamp (254 nm).

In the exemplary experiment, bactericidal killing efficacy of the exemplary excilamps was tested, for example, on methicillin resistant *Staphylococcus aureus* (MRSA). MRSA can be the cause of about 25% of surgical site infection and can be associated with approximately 20,000 deaths per year in the United States, mostly healthcare related. MRSA and antibiotic-susceptible *S. aureus* are typically equally susceptible to UV from conventional germicidal lamps. (See, e.g., Conner-Kerr T A, Sullivan P K, Gaillard J, Franklin M E, Jones R M. *The effects of ultraviolet radiation on antibiotic-resistant bacteria in vitro. Ostomy Wound Manage.* 1998; 44(10):50-6). The exemplary results are shown, for example, in FIG. 8, indicating that at an excilamp fluence of about 100 mJ/cm$^2$, an MRSA survival level of $10^{-4}$ can be achieved. For example, FIG. 8 shows an exemplary graph of MRSA (strain US300) inactivation after exposure to UV from the exemplary filtered KrBr or KrCl excilamps (207 nm and 222 nm, respectively).

Figure 8:
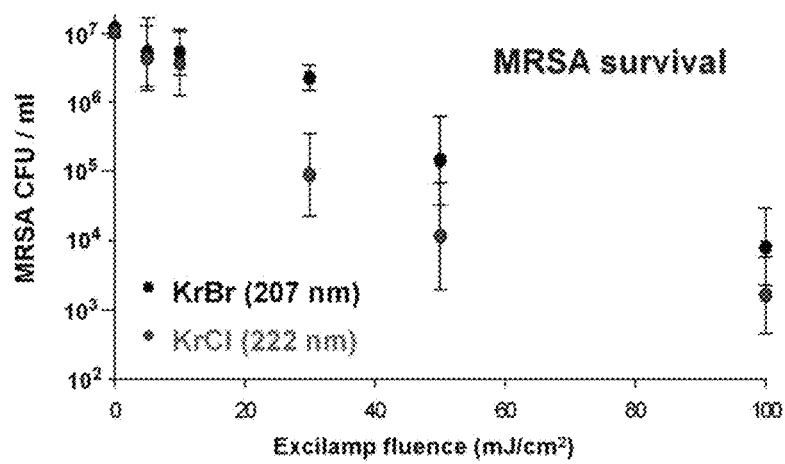
FIG. 8 is a graph of MRSA survival with respect to an excilamp fluence according to certain exemplary embodiments of the present disclosure.

Comparing the exemplary results in FIGS. 7 and 8, the exemplary filtered excilamp UV radiation at 207 nm and at 222 nm can differentially effect and/or kill MRSA relative to the human cells. For example, at exemplary filtered excilamp fluences of about 100 mJ/cm$^2$, the survival level of human cells is, for example, in the range of about 0.1 to 1, while the survival level of MRSA is in the range of about $10^{-4}$. Such exemplary finding are in considerable contrast to the situation for convention germicidal UV lamps (GUVL), which is roughly equally efficient at killing bacteria and human cells. For example, for a conventional germicidal UV lamp, at a UV fluence for which a GUVL produces a bacterial survival of $10^{-4}$, the human cell survival from the GUVL is about $0.3 \times 10^{-4}$, a human cell survival advantage of 0.3. With the exemplary excilamp at 207 or 222 nm, at a UV fluence for which the exemplary 207 or 222 nm filtered excilamp produces a bacterial survival of $10^{-4}$, the human cell survival by the exemplary filtered exilamps is in the range of about 0.1 to 1, a human cell survival advantage in the range of 5,000.

Exemplary Induction of Pre-Mutagenic DNA Lesions in Human Skin

Figure 9A:
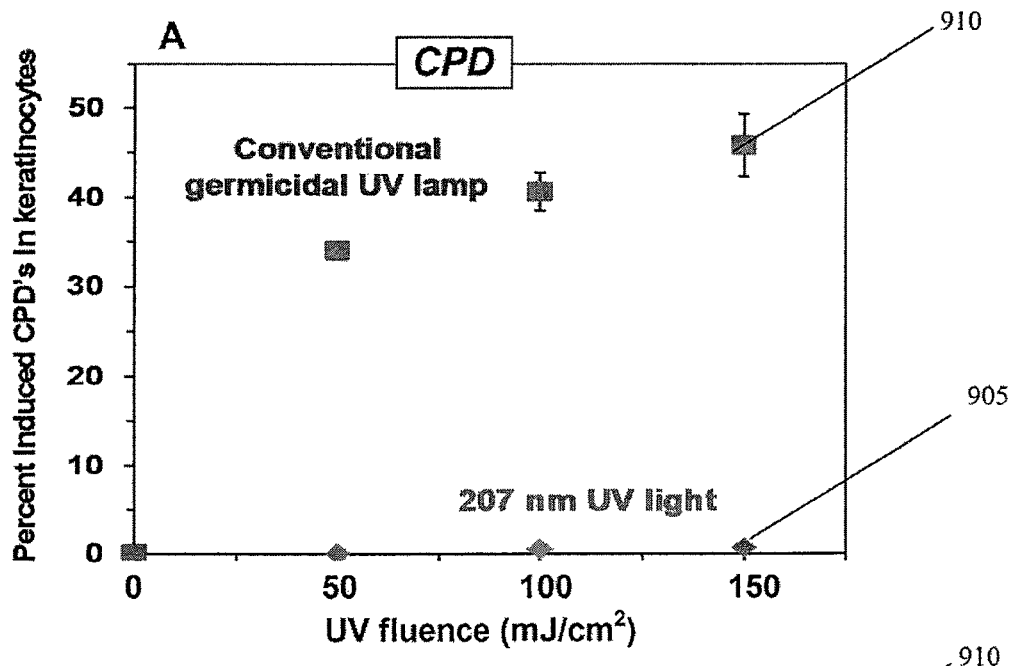
FIG. 9(a) is a graph of exemplary yields for pre-mutagenic DNS lesions for cyclobutane pyrimidine dimers.
Figure 9B:
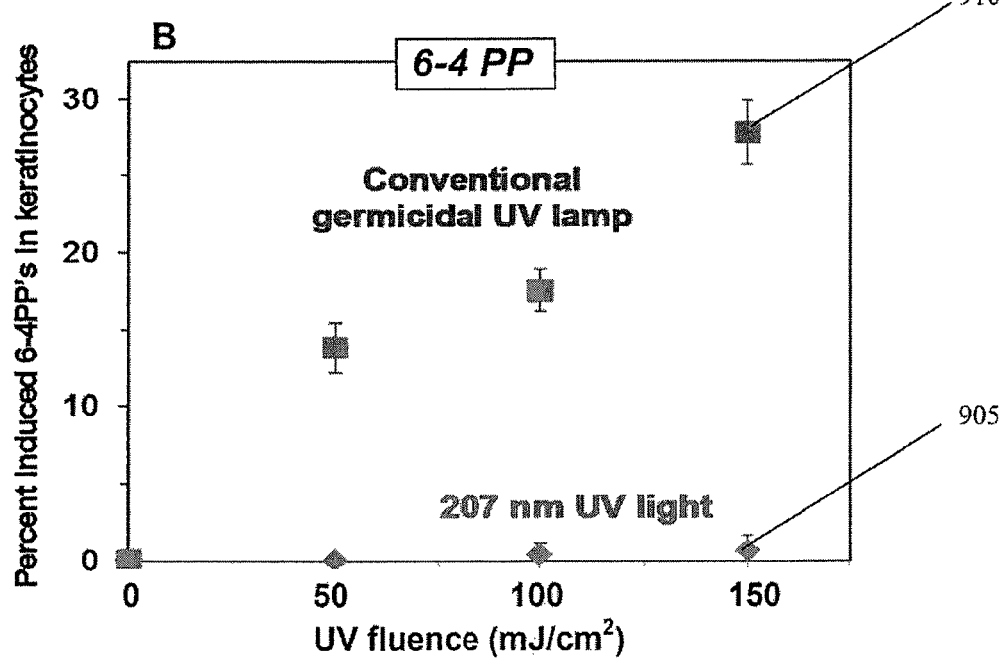
FIG. 9(b) is a graph of exemplary yields for pre-mutagenic DNS lesions for pyrimidine-pyrimidone 6-4 photoproducts (6-4PP).

FIGS. 9(*a*) and 9(*b*) illustrate the exemplary measured induced yields of cyclobutane pyrimidine dimers (CPD) lesions (FIG. 9(*a*)) and 6-4 photoproducts (6-4PP, FIG. 9(*b*)) after exposure of the exemplary 3-D skin tissue model to the broad UV spectrum from a conventional germicidal UV lamp (e.g., peak 254 nm) or to an exemplary 207-nm light 905 from the Kr—Br excimer lamp. The exemplary germicidal lamp produced high yields of both pre-mutagenic skin DNA lesions. However after 207-nm exposure, neither lesion showed an induced yield which was significantly elevated above zero, at any of the studied fluences.

The exemplary 207-nm light can kill MRSA much more efficiently than it can kill human cells. For example at a fluence of approximately 207-nm, the light can produce four logs of MRSA cell kill, and there is much less than one decade of cell kill in human cells. In contrast with the results for 207-nm light, while conventional germicidal lamps 910 can efficiently kill MRSA, conventional germicidal lamps are also almost as efficient at killing human cells. Quantitatively, for a four-log level of MRSA killing, 207-nm UV light can produce about 1,000-fold less human cell killing than a conventional germicidal UVC lamp.

In terms of the safety of 207-nm UV light, the lack of induction of typical UV-associated pre-mutagenic DNA lesions in the epidermis of a 3-D skin model is consistent with biophysical expectations based on the limited penetration of 207-nm UV light, and consistent with earlier studies using 193-nm laser light. (See, e.g., Green H, Boll J, Parrish J A, Kochevar I E, Oseroff A R (1987) Cytotoxicity and mutagenicity of low intensity, 248 and 193 nm excimer laser radiation in mammalian cells. Cancer Res 47: 410-413). While other UV wavelengths have been suggested as potentially being safe for human exposure, in particular 405 nm (see, e.g., McDonald R S, Gupta S, Maclean M, Ramakrishnan P, Anderson J G, et al. (2013) 405 *nm Light exposure of osteoblasts and inactivation of bacterial isolates from arthroplasty patients: potential for new disinfection applications?* Eur Cell Mater 25: 204-214) and 254 nm (see, e.g., Dai T, Vrahas M S, Murray C K, Hamblin M R (2012) *Ultraviolet C irradiation: an alternative antimicrobial approach to localized infections?* Expert Rev Anti Infect Ther 10: 185-195), no mechanisms have been proposed for a differential toxic effect for bacteria vs. human cells at these wavelengths, and both 405-nm light (see, e.g., Papadopoulo D, Guillouf C, Mohrenweiser H, Moustacchi E (1990) *Hypomutability in Fanconi anemia cells is associated with increased deletion frequency at the HPRT locus.* Proc Natl Acad Sci USA 87: 8383-8387) and 254-nm light (see, e.g., Zolzer F, Kiefer J (1984) *Wavelength dependence of inactivation and mutation induction to 6-thioguanine-resistance in V79 Chinese hamster fibroblasts.* Photochem Photobiol 40: 49-53) have been shown to be mutagenic to mammalian cells at relevant fluences.

In contrast, the exemplary 207-nm light from a Kr-Br excimer lamp can have considerable potential for safely reducing SSI rates. Such lamps can be used in an operating room environment without the need for protective clothing for the staff or the patient. For example, 207-nm light can be used for continuous low-fluence-rate exposure during a surgical procedure, because current evidence suggests that the majority of SSI can result from bacteria alighting directly onto the surgical wound from the air. Evidence for the dominance of an airborne route can come from correlations between the density of airborne bacteria and post-operative sepsis rates. (See, e.g., Lidwell O M, Lowbury E J, Whyte W, Blowers R, Stanley S J, et al. (1983) *Airborne contamination of wounds in joint replacement operations: the relationship to sepsis rates.* J Hosp Infect 4: 111-131; Gosden P E, MacGowan A P, Bannister G C (1998) *Importance of air quality and related factors in the prevention of infection in orthopaedic implant surgery.* J Hosp Infect 39: 173-180). Evidence for the significance of airborne bacteria alighting directly on the surgical wound can come from, for example, studies of conventional UV lamps specifically directed over the surgical site (see, e.g., Ritter M A, Olberding E M, Malinzak R A (2007) Ultraviolet lighting during orthopaedic surgery and the rate of infection. J Bone Joint Surg Am 89: 1935-1940), and also wound-directed filtered airflow studies. (See, e.g., Stocks G W, O'Connor D P, Self S D, Marcek G A, Thompson B L (2011) *Directed air flow to reduce airborne particulate and bacterial contamination in the surgical field during total hip arthroplasty.* J Arthroplasty 26: 771-776).

Thus, a continuous low-fluence-rate exposure of 207-nm UV light onto the surgical wound area during the complete surgical procedure can kill bacteria as they alight onto the wound area. Such exemplary continuous exposure can be designed to inactivate bacteria before the bacteria can penetrate into the interior of the wound. A second advantage associated with targeting bacteria as the bacteria alight onto the wound area is in relation to biofilms. (See, e.g., Frei E, Hodgkiss-Harlow K, Rossi P J, Edmiston C E, Jr., Bandyk D F (2011) *Microbial pathogenesis of bacterial biofilms: a causative factor of vascular surgical site infection.* Vasc Endovascular Surg 45: 688-696). For example, as bacteria can alight onto the skin/wound, they can typically be in individual planktonic form, and thus, can be amenable to killing by 207-nm light. This can prevent the subsequent formation of bacterial clusters (e.g., biofilms), which can be refractory to 207-nm light as they are to most other therapies.

Several configurations for the exemplary 207-nm lamp in a surgical setting can be possible. It is important that surgical staff do not inadvertently block the UV light, so one exemplary arrangement can be for the excimer lamp to be incorporated into a standard overhead surgical illumination system. A possible second exemplary UV light source, to ensure a level of redundancy from inadvertent shielding, can be incorporation into a surgeon's headlight illumination system, with the UV light transmitted to the headlight via fiber optics. (See, e.g., Miller J, Yu X-B, Yu P K, Cringle S J, Yu D-Y (2011) *Development of a fiber-optic delivery system capable of delivering 213 and 266 nm pulsed Nd:YAG laser radiation for tissue ablation in a fluid environment.* Appl Opt 50: 876-885).

Commercial 207-nm excimer lamps can be inexpensive and long lived. In fact in a different wavelength range (e.g., 172 nm) xenon excimer lamps (see, e.g., Salvermoser M, Murnick D E (2003) *High-efficiency, high-power, stable 172 nm xenon excimer light source.* Appl Phys Lett 83: 1932-1934) with rated lifetimes of 50,000 to 100,000 hours, are already in commercial use (see, e.g., Hitzschke L, Vollkommer F (2001) Product families based on dielectric barrier discharges. In: Bergman R S, editor. Proceedings of the Ninth International Symposium on the Science & Technology of Light Sources (LS:9). Ithaca, N.Y.: Cornell University Press. pp. 411-421), providing (e.g., using appropriate phosphors) both interior and exterior office lighting, for example on the Rotterdam KPN Telecom tower. (See, e.g., Tscherteu G, Lervig M C, Brynskov M KPN Tower, Rotterdam, 2000; 2012; Aarhus, Denmark. Media Architecture Institute Vienna/Sydney and Aarhus University).

In addition to direct bactericidal applications in surgical environments, the exemplary 207-nm UV light can be used to treat, on a continuous basis, any airborne environment where there is a high likelihood of airborne-based pathogen transmission (e.g., Tuberculosis or the pandemic influenza). While upper-room UV irradiation systems have long been considered, based on conventional broad-spectrum UV lamps (see, e.g., Reed N G (2010) *The history of ultraviolet germicidal irradiation for air disinfection.* Public Health Rep 125: 15-27), and have shown some promise(see, e.g., Nardell E A, Bucher S J, Brickner P W, Wang C, Vincent R L, et al. (2008) *Safety of upper-room ultraviolet germicidal air disinfection for room occupants: results from the Tuberculosis Ultraviolet Shelter Study.* Public Health Rep 123: 52-60; Escombe A R, Moore D A, Gilman R H, Navincopa M, Ticona E, et al. (2009) *Upper-room ultraviolet light and negative air ionization to prevent tuberculosis transmission.* PLoS Med 6: e43), they have not, however, been widely used, in part, because of safety concerns relating to potential low-level broad-spectrum UV exposure. (See, e.g., Nardell E A, Bucher S J, Brickner P W, Wang C, Vincent R L, et al. (2008) *Safety of upper-room ultraviolet germicidal air dis-* infection for room occupants: results from the Tuberculosis Ultraviolet Shelter Study. Public Health Rep 123: 52-60; Wengraitis S, Reed N G (2012) *Ultraviolet spectral reflectance of ceiling tiles, and implication for the safe use of upper-room ultraviolet germicidal irradiation. Photochem Photobiol* 88: 1480-1488; Sliney D (2013) *Balancing the risk of eye irritation from UV-C with infection from bioaerosols. Photochem Photobiol* 89: 770-776).

Figure 5:
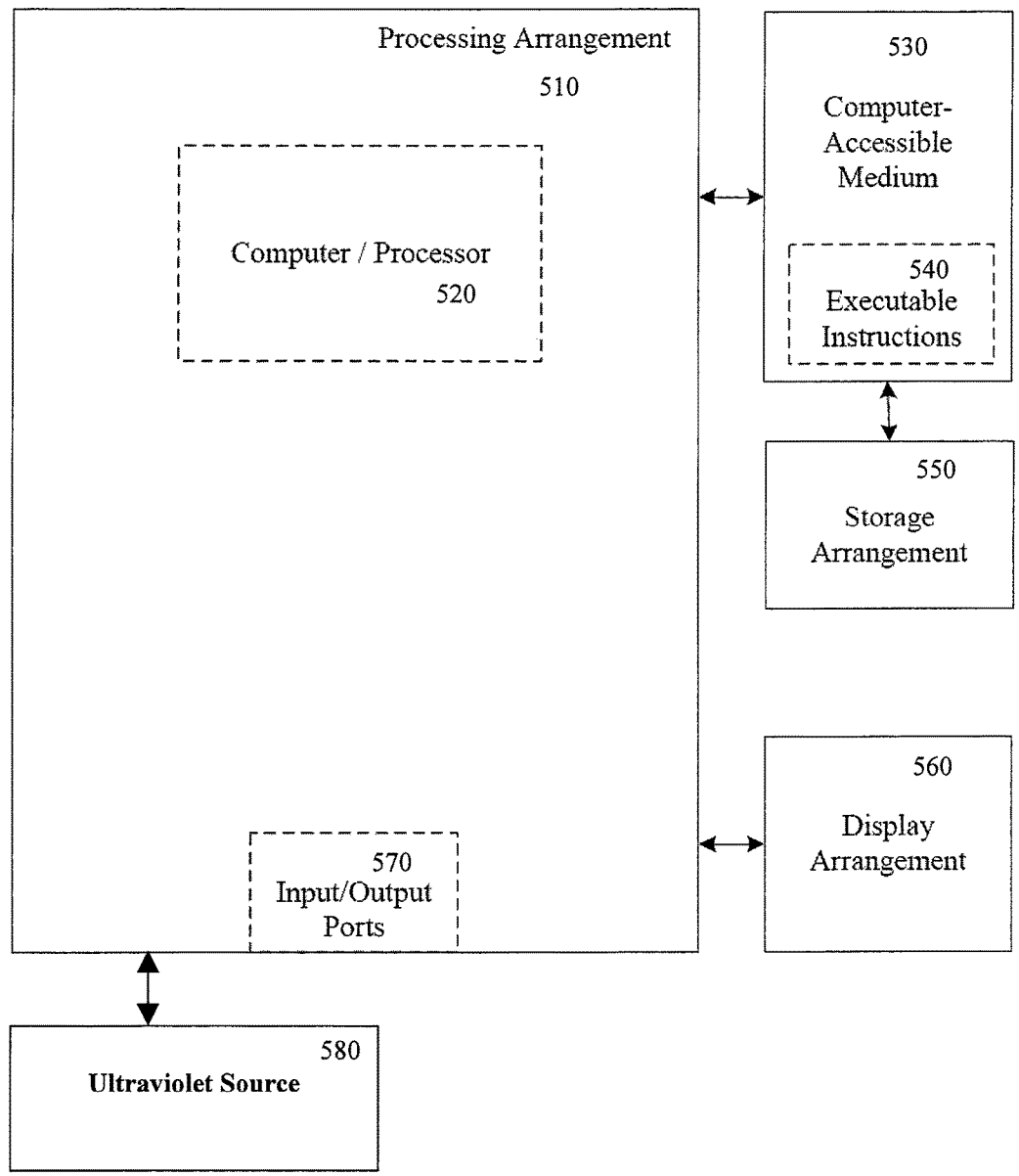
FIG. 5 is an exemplary block diagram of an apparatus according to particular exemplary embodiments of the present disclosure.

FIG. 5 shows an exemplary block diagram of an exemplary embodiment of a system according to the present disclosure. For example, exemplary procedures in accordance with the present disclosure described herein can be performed by or controlled using a UV generation source 580 and/or hardware processing arrangement and/or a computing arrangement 510, separately and in conjunction with one another. Such exemplary processing/computing arrangement 510 can be, e.g., entirely or a part of, or include, but not limited to, a computer/processor 520 that can include, e.g., one or more microprocessors, and use instructions stored on a computer-accessible medium (e.g., RAM, ROM, hard drive, or other storage device).

As shown in FIG. 5, e.g., a computer-accessible medium 530 (e.g., as described herein above, a storage device such as a hard disk, floppy disk, memory stick, CD-ROM, RAM, ROM, etc., or a collection thereof) can be provided (e.g., in communication with the processing arrangement 510). The computer-accessible medium 530 can contain executable instructions 540 thereon. In addition or alternatively, a storage arrangement 550 can be provided separately from the computer-accessible medium 530, which can provide the instructions to the processing arrangement 510 so as to configure the processing arrangement to execute certain exemplary procedures, processes and methods, as described herein above, for example.

Further, the exemplary processing arrangement 510 can be provided with or include an input/output arrangement 570, which can include, e.g., a wired network, a wireless network, the internet, an intranet, a data collection probe, a sensor, etc. As shown in FIG. 5, the exemplary processing arrangement 510 can be in communication with an exemplary display arrangement 560, which, according to certain exemplary embodiments of the present disclosure, can be a touch-screen configured for inputting information to the processing arrangement in addition to outputting information from the processing arrangement, for example. Further, the exemplary display 560 and/or a storage arrangement 550 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. In addition, all publications and references referred to above can be incorporated herein by reference in their entireties. It should be understood that the exemplary procedures described herein can be stored on any computer accessible medium, including a hard drive, RAM, ROM, removable disks, CD-ROM, memory sticks, etc., and executed by a processing arrangement and/or computing arrangement which can be and/or include a hardware processors, microprocessor, mini, macro, mainframe, etc., including a plurality and/or combination thereof. In addition, certain terms used in the present disclosure, including the specification, drawings and claims thereof, can be used synonymously in certain instances, including, but not limited to, e.g., data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it can be explicitly being incorporated herein in its entirety. All publications referenced can be incorporated herein by reference in their entireties.

What is claimed is:

1. A method for selectively killing or destroying at least one bacteria at a medical treatment site or in a medical treatment environment, comprising:
    generating, with at least one excilamp, at least one bactericidal radiation configured to selectively kill or destroy the at least one bacteria on or within a body, while avoiding harm to cells of the body, wherein the at least one bactericidal radiation has at least one wavelength that is in a range of 190 nanometers (nm) to 230 nm, and wherein a peak wavelength of the at least one bactericidal radiation is at least one of approximately at 207 nm or approximately at 222 nm;
    filtering, with a filter arrangement comprising at least one of a band pass filter or a combination of a low pass filter and a high pass filter, the at least one bactericidal radiation to prevent all ultraviolet wavelengths that are outside of the range from passing through the filter arrangement;
    allowing all wavelengths in the range of 190 nm to 230 nm to be provided to the body;
    fluorescing visible light to indicate that the at least one excilamp is operating; and
    irradiating the at least one bacteria using the allowed wavelengths and selectively killing or destroying the at least one bacteria.

2. The method of claim 1, further comprising directing the at least one bactericidal radiation using the at least one excilamp.

3. The method of claim 1, wherein the at least one excilamp includes at least one of a krypton-bromine lamp or a krypton-chlorine lamp.

4. The method of claim 1, wherein the filter arrangement includes at least one of a chemical filter or a dielectric filter.

5. The method of claim 1, wherein the filtering the at least one bactericidal radiation to prevent all ultraviolet wavelengths that are outside of the range from passing through the filter arrangement includes filtering out the at least one bactericidal radiation that has a peak wavelength outside of the range.

6. The method of claim 1, wherein the selectively killing or destroying the at least one bacteria includes, at a same time, avoiding harm to cells of the body.

7. The method of claim 6, wherein the allowing all wavelengths in the range of 190 nm to 230 nm comprises allowing every allowed wavelength to pass therethrough.

8. The method of claim 1, further comprising providing the at least one bactericidal radiation from within a housing through a window thereof in a first direction that is approximately parallel to a second direction of irradiation of the at least one radiation through the window.

9. The method of claim 1, further comprising providing the at least one bactericidal radiation from within a housing through a window thereof in a first direction that is approximately parallel to a second direction of irradiation of the at least one radiation through the window.

10. The method of claim 1, wherein the allowing all wavelengths in the range of 190 nm to 230 nm comprises allowing every allowed wavelength to pass therethrough.

11. The method according to claim 1, wherein at least one of bacteria has a cell diameter that is less than 1 μm, and wherein the generation or the filtering comprises modifying the at least one bactericidal radiation to penetrate and kill the at least one, and preventing a penetration of a nucleus of human cells that are approximately at a diameter of 10 μm and 30 μm.

* * * * *